(12) United States Patent
Kopreski et al.

(10) Patent No.: US 6,849,616 B1
(45) Date of Patent: Feb. 1, 2005

(54) METHODS TO POTENTIATE INTRAVENOUS ESTRAMUSTINE PHOSPHATE

(75) Inventors: Michael S. Kopreski, Portage, MI (US); Beryl Asp, Helsingborg (SE); Bo Fredholm, Helsingborg (SE); Per-Olv Gunnarsson, Helsingborg (SE)

(73) Assignee: Pharmacia Italia S.p.A., Milan (IT)

( * ) Notice: Subject to any disclaimer, the term of this patent is extended or adjusted under 35 U.S.C. 154(b) by 795 days.

(21) Appl. No.: 09/276,741

(22) Filed: Mar. 26, 1999

Related U.S. Application Data
(60) Provisional application No. 60/079,542, filed on Mar. 27, 1998.

(51) Int. Cl.$^7$ .............................................. A61K 31/56
(52) U.S. Cl. ..................................................... 514/182
(58) Field of Search ........................................ 514/182

(56) References Cited

U.S. PATENT DOCUMENTS

| | | | |
|---|---|---|---|
| 4,584,136 A | 4/1986 | Yoshida et al. ............ 260/397.5 |
| 5,077,056 A | 12/1991 | Bally et al. | |
| 5,424,073 A | * 6/1995 | Rahman et al. .............. 424/450 |
| 5,616,341 A | 4/1997 | Mayer et al. | |
| 5,728,687 A | 3/1998 | Bissery ......................... 514/90 |
| 5,780,446 A | * 7/1998 | Ramu ............................ 514/34 |
| 5,795,882 A | * 8/1998 | Bishop et al. ............... 514/170 |

OTHER PUBLICATIONS

A. Yagoda et al, *Journal of Urology*, vol. 145, p. 384A, Abstract 686 (1991).
S. B. Andersson, et al, *Acta Pharm Suecica*, vol. 19, pp. 1–10 (1962).
S. Batra, et al, *Int. J. Cancer*, vol. 68, pp. 644–649 (1996).
A.T. Bergenheim, et al, *Br. J. Cancer*, vol. 67, pp. 358–361 (1993).
J. Bergh, et al, *Cancer Res.*, vol. 48, pp. 4615–4619 (1988).
P. Björk, et al, *Anticancer Res.*, vol. 11(3), pp. 1173–1182 (1991).
P. Björk, et al, *Pancreas*, vol. 6, No. 1, pp. 1:77–89 (1991).
B. Dahllöf, et al, *Cancer Res.*, vol. 53, pp. 4573–4581 (1993).
M. Edgren, et al, *Acta Oncologica*, vol. 35(4), pp. 483–488 (1996).
S. Eklöv, et al, *The Prostate*, vol. 20, pp. 43–50 (1992).
S. Eklöv, et al, *Anticancer Res.*, vol. 16(4A), pp. 1819–1822 (1996).
S. Flütchter, et al, *The Prostate*, vol. 14, pp. 27–43 (1989).
B. Forsgren, et al, *Proc. Natl. Acad. Sci., USA*, vol. 76, pp. 3149–3153 (1979).
P. O. Gunnarson, et al, *Eur. J. Clin. Pharmacol.*, vol. 26, pp. 113–119 (1984).
P. O. Gunnarsson, et al, *Scand. J. Urol. Nephrol.*, vol. 15, pp. 201–206 (1981).

(List continued on next page.)

*Primary Examiner*—Barbara P. Badio
(74) *Attorney, Agent, or Firm*—McDonnell Boehnen Hulbert & Berghoff LLP

(57) ABSTRACT

Estramustine phosphate is an anti-mitotic chemotherapeutic drug with proven efficacy against cancer. The invention describes methods which potentiate the therapeutic benefit of intravenous estramustine phosphate. The invention provides for intravenous estramustine phosphate to be administered at a high dosage exceeding 1300 mg as a single dose. Efficacious enhancement of estramustine phosphate pharmacokinetics is thereby achieved. Further provided, estramustine phosphate may be intravenously administered for use in combinational regimens with other chemotherapeutic agent. The therapeutic advantages achieved using the intravenous estramustine phosphate formulation are applicable to treatment of a variety of cancers including prostate cancer, breast cancer, lung cancer, colorectal cancer, pancreatic cancer, ovarian cancer, melanoma, and other cancers.

11 Claims, 2 Drawing Sheets

OTHER PUBLICATIONS

B. Hartley–Asp, *The Prostate*, vol. 5, pp. 93–100 (1984).
B. Hartley–Asp, et al. *J. Urology*, vol. 127, pp. 818–822 (1982).
G. Hudes, et al, *Seminars Oncology*, vol. 22, No. 3, Suppl. 6, pp. 6–11 (1995).
G. R. Hudes, et al, *J. Clin. Oncology*, vol. 10, No. 11, pp. 1754–1761 (1992).
S. Keren–Rosenberg, et al, *Seminars in Oncology*, vol. 24, No. 1, Suppl. 3, pp. S3–26 to S3–29 (1997).
B. Lindberg, *Journal of Urology*, vol. 108, pp. 303–305 (1972).
U. Maier, et al, *Eur. Urol.*, vol. 17, 216–218 (1990).
M. M. Mareel, et al, *Cancer Res.*, vol. 48, pp. 1842–1849 (1988).
G. P. Murphy et al, *Seminars in Oncology*, vol. 10, No. 3, Suppl 3, pp. 34–42 (1983).
R. Nagel, et al, *British Journal of Urology*, vol. 49, pp. 73–79 (1977).
B. J. Norlén, et al, *Journal of Urology*, vol. 140, pp. 1058–1062 (1988).
D. P. Petrylak, *Cancer Investigation*, vol. 16, Supp 1, p. 62–63 (1997).
K. J. Pienta, et al, *Journal of Urology*, vol. 149, pp. 1622–1625 (1993).
K. J. Pienta, et al, *J. Clinical Oncology*, vol. 12, No. 10, pp. 2005–2012 (1994).
A. D. Seidman, et al, *J. Urology*, vol. 147, pp. 931–934 (1992).
L. A. Speicher, *Cancer Res.*, vol. 52, pp. 4433–4440 (1992).
M. E. Stearns, et al, *J. Cell Science*, vol. 89, pp. 331–342 (1988).
E. von Schoultz, et al, *Melanoma Res.*, vol. 4(6), pp. 401–405 (1994).
P. H. Walz, et al, *Akt. Urol.*, vol. 27, pp. 92–93 (1996).
G Hudes et al, *Journal of Clinical Oncology*, vol. 20, No. 4, pp. 1115–1127 (2002).
E Hovey et al, *American Society of Clinical Oncology*, #2424 (Abstract only) (2001).
S Talbot et al, *American Society of Clinical Oncology*, #437 (Abstract only) (2000).
M. R. Smith et al., *American Society of Clinical Oncology*, #137 (Abstract only) (1999).
P Kim et al, *American Society of Clinical Oncology*, #509 (Abstract only) (1999).
D Panda et al, *Proc. Natl. Acad. Sci. USA*, vol. 94, pp. 10560–10564 (1997).
U. Maier et al, *Eur Urol*, vol. 17, pp. 216–218 (1990).
B. Hartley–Asp et al, *Proc. Am. Soc. Clin. Onc.*, vol. 20, p. 183a (2001).
Examination Report issued in Israel Patent Application No. 133,612 on Nov. 10, 2002, with attached English translation of the Substantive Portion, (English translation only).
Keren–Rosenberg et al, *Semin. Oncol.*, vol. 24 (1), Suppl. 3, pp. S3/26–S3/29 (1997), Database Chemical Abstracts on STN, Abstract No. 126:271944, (Abstract only).
Keren–Rosenberg et al, *Proc. Am. Soc. Clin. Oncol.* vol. 15, p. 181 (1996),Database Drugu on STN, Abstract No. 96–40815, (Abstract only).
Hudes et al, *Semin. Oncol.*, vol. 22 (5), Suppl. 12, pp. 41–45 (1995), Database Chemical Abstracts on STN, Abstract No. 124:105826, (Abstract only).
Pitenta, *J. Urol.*, vol. 149, No. 4, Suppl. 428 A (1993), Database Drugu on STN, Abstract No. 93–26752, (Abstract only).
Hudes, et al., "Paclitaxel Plus Estramustine in Metastatic Homrone–Refractory Prostate Cancer", Seminars in Oncology, vol. 22, No. 5, suppl. 12, pp. 41–45 (1995).
Garcia, et al., "Phase I and Pharmacologic Study of Estramustine Phsophate and Short Infusions of Paclitaxel in Women with Solid Tumors", Journal of Clinical Oncology, vol. 16, No. 9, pp. 2959–2963 (1998).

\* cited by examiner

METHODS TO POTENTIATE INTRAVENOUS ESTRAMUSTINE PHOSPHATE

This application claims priority to U.S. Provisional Application serial No. 60/079,542, which was filed on Mar. 27, 1998.

BACKGROUND OF THE INVENTION

1. Field of the Invention

The present invention relates to the use of estramustine phosphate, a non-nitrogen mustard carbamate derivative of estradiol-17b-phosphate, as a high dose infusion. The present invention further relates to methods to potentiate intravenously administered estramustine phosphate and to methods for treating cancer by intravenously administering estramustine phosphate.

2. Discussion of the Background

Cytotoxic effects have been shown to be due to the intact estramustine molecule (Hartley-Asp, 1982). Tissue culture studies have shown that estramustine (EM) is an anti-mitotic agent, causing a dose-dependent blocking of tumor cell division in the metaphase (Hartley-Asp, 1984). Metaphase arrest is known to be caused by an interference of drugs with the microtubule structure that forms the mitotic spindle. It has been shown, with the help of immunohistochemistry, that dose-dependent disturbances of interphase microtubules occur in cultured human prostatic cells (Mareel 1988, Dahllof 1993). Treatment with EM in vitro inhibited the assembly of microtubules composed of only tubulin demonstrating a direct interaction with tubulin (Dahllof 1993). In addition, an interaction with microtubule associated proteins (MAPs) has been demonstrated (Stearns 1988). MAPs are high molecular weight proteins that are believed to be important in stabilizing microtubules. That EM exhibits the mechanism of action of an anti-mitotic agent has been confirmed in vivo (Eklöv, 1992).

Estramustine phosphate is thus an anti-mitotic agent currently used in the treatment of advanced adenocarcinoma of the prostate. As a single agent, its activity in hormone-refractory prostate cancer is comparable to that of several other cytotoxic agents that have been studied in a series of multi-institutional, randomized trials by the National Prostatic Cancer Project (Murphy, 1983). While the drug is usually administered orally at a dose of 10–15 mg/kg/day, it is approved for intravenous administration in several countries. However, estramustine phosphate when administered intravenously has been used at dosages and according to a schedule paralleling the oral administration for the drug, i.e. at recommended dosages of 300–600 mg daily given intravenously and usually repetitively over for several consecutive days. This is then followed by orally administered drug.

In the published material, details from about 500 patients who have been treated with the intravenous formulation initially which was then followed by oral treatment can be found. Induction schedules employing 300–600 mg intravenous daily for 7–21 days, followed by daily oral doses, were typical in these studies. The drug was administered as a slow intravenous injection or as a bolus at 300 mg/day, and thrombophlebitis and local irritation at the peripheral intravenous injection sites were considered major limitations of drug administration requiring the establishment of central line administration in many patients or discontinuation of treatment. At 450 mg/day, Nagel and Kölln (1977) stated that this led to so "severe gastrointestinal problems that 300 mg/day was taken as the maximum intravenous daily dose." In a compilation, by Andersson et al, of 245 patients recevn 300–600 mg/day for 21 days followed by the same dose once or twice weekly for 2 months, 20% of the patients exhibited thrombophlebitis, 17% exhibited gastrointestinal problems and 9% exhibited liver disturbances. Toxicities resulting from such repetitive dosing schedules often require drug discontinuation (Lundgren, 1995). Maier (1990), administered daily intravenous doses of 900 mg/day for 7–10 days, followed by oral therapy, without reporting phlebitis but severe liver problems did occur in 11 of 18 patients (61%) with one death due to toxic liver failure.

The state of the art thus typically utilized intravenous estramustine phosphate formulations as a single-agent method for initiating a long term oral estramustine therapy. Furthermore, intravenous administration of estramustine phosphate at higher dosages is generally considered prohibitive due to toxicity. It is neither known nor obvious to the art that single dose, high-dosage administration of estramustine phosphate is feasible intravenously. While dosing up to 1200 mg/m$^2$ have been given orally (Keren-Rosenberg, 1997), differences in drug metabolism and bioavailability do not permit extrapolation to the high dose intravenous formulation, with relative bioavailability of estromustine after oral administration found to be only 44%, (Gunnarsson, 1984), with the phosphate moiety dephosphorylated in the oral formulation in contrast to the intravenous formulation. Furthermore, it is not known in the art that intravenous estramustine phosphate can be used in combinational chemotherapy regimens, including the use of higher dose intravenous estramustine phosphate. Furthermore, it is not known to the art that intravenous estramustine phosphate has clinical utility for cancers other than for the prostate cancer indication.

In previous work, Dr. Beryl Hartley-Asp, a co-inventor of this invention, was the first to recognize the synergistic potential of estramustine phosphate with other cytotoxic agents. (Mareel 1988). In several experiments, it was demonstrated that prolonged exposure to estramustine was necessary to achieve potentiation. Consequently, daily dosing was deemed necessary leading to the use of the ORAL preparation as previous data from the intravenous (IV) preparation suggested that achievement of constant high levels would not be clinically achievable with IV dosing.

Additive and possibly synergistic antimicrotubule effects in cells in vitro have been shown for estramustine and many other cytotoxic agents, (Mareel 1988, Speicher 1992, Pienta 1993, Batra,1996). Thus, the combination of estramustine phosphate with other drugs in humans has been carried out using ORAL administration of estramustine phosphate. Phase II trials (Seidman, 1992,.Hudes, 1992, Pienta, 1994, Hudes, 1996) with Estramustine phosphate combined with vinblastine, have been carried out in hormone refractory prostate cancer. In these trials a 50–75% decrease in prostate specific antigen was demonstrated among 88 patients. The most frequent toxicity was mild to moderate nausea. Of particular note is the 10.5% (4/37) incidence of significant cardiovascular toxicity including one deep venous thrombosis (DVT), one myocardial infarction, one episode of congestive heart failure, and one reversible neurologic event which required stopping therapy in these patients and which can be attributed to estramustine phosphate. In another Phase II trial carried out by Pienta et al (1994), estramustine phosphate (oral) was combined with Etoposide. Fifty two patients were evaluable; including 20 patients with soft tissue disease, in which 3 complete responses (CR) (15%) and 6 partial responses (PR) (30%) were observed. In 32 patients with bone metastases 8 patients improved (25%), and 12 patients were stable (38%). Overall 13 men (25%)

had a 75% decrease in prostate specific antigen, and 28 men (54%) had a 50% decrease. A Phase I–II study of Taxol (Hudes, 1992) and estramustine phosphate was carried out in seventeen patients with hormone refractory prostate cancer. Six patients had measurable disease and 3 of these obtained a PR of 2+, 6, and 8 months. Prostate specific antigen (PSA) decreased by $\geq 50\%$ in 58.8%. Median duration of response was 7 months. Grade 3–4 granulocytopenia and mucositis occurred in 2 patients, nausea grade 1–2 (70.5%) and grade 3 in one patient. Edema was seen in 8 patients (47%) and transient hepatic enzyme elevation of grade 1–3 in 6 patients (35.2%).

In a recent study, Petrylak et al., (1997), using escalating doses of docetaxel with estramustine phosphate given orally demonstrated an overall prostate specific antigen response rate of 62%. In patients with bidimensionally measurable disease, 3 (43%) achieved a partial response in lymph nodes, and 1 achieved a minor response in ischial mass. This demonstrates that combination treatment with ORAL estramustine phosphate is efficacious. However, combinations of intravenous estramustine phosphate with these cytotoxic agents are not known to the art. Differences in the metabolism, particularly regarding the phosphate moiety, in the oral versus intravenous estramustine phosphate formulations make combinational therapies with the intravenous formulation non-obvious.

In contrast to other anti-mitotic agents, the effect of estramustine phosphate appears to be dependent on the presence of the estramustine binding protein (EMBP) (Eklöv, 1996). This is found under normal conditions only in the prostate (Forsgren, 1979, Flucher, 1989). However, a similar protein has also been identified in many cancerous tissues, as well as prostate tumors, such as lung, breast glioma, colon, pancreas (Björk, 1991, Bergh 1988, Eklöv 1996, Edgren 1996, Von Schoultz, 1994, Bergenheim, 1993). This protein binds estra- and estro-mustine (EaM and EoM) with very high affinity and is thought to be responsible for the selective retention of EoM in the prostate tumor, where a ratio of 1:6 to 1:11 plasma/tumor has been found in prostate cancer patients treated with estramustine phosphate oral and intravenously, respectively (Norlen 1988,Walz 1988). Recently, we have demonstrated a correlation between the levels of EMBP and the levels of EaM and EoM in human prostate tumors after a single intravenous estramustine phosphate dose to patients before radical prostatectomy, indicating that EMBP could be the cause of drug retention (Walz, 1996).

BRIEF DESCRIPTION OF THE FIGURES

A more complete appreciation of the invention and many of the attendant advantages thereof will be readily obtained as the same become better understood by reference to the following detailed description when considered in connection with the accompanying drawings, wherein.

SUMMARY OF THE INVENTION

Figure 1:
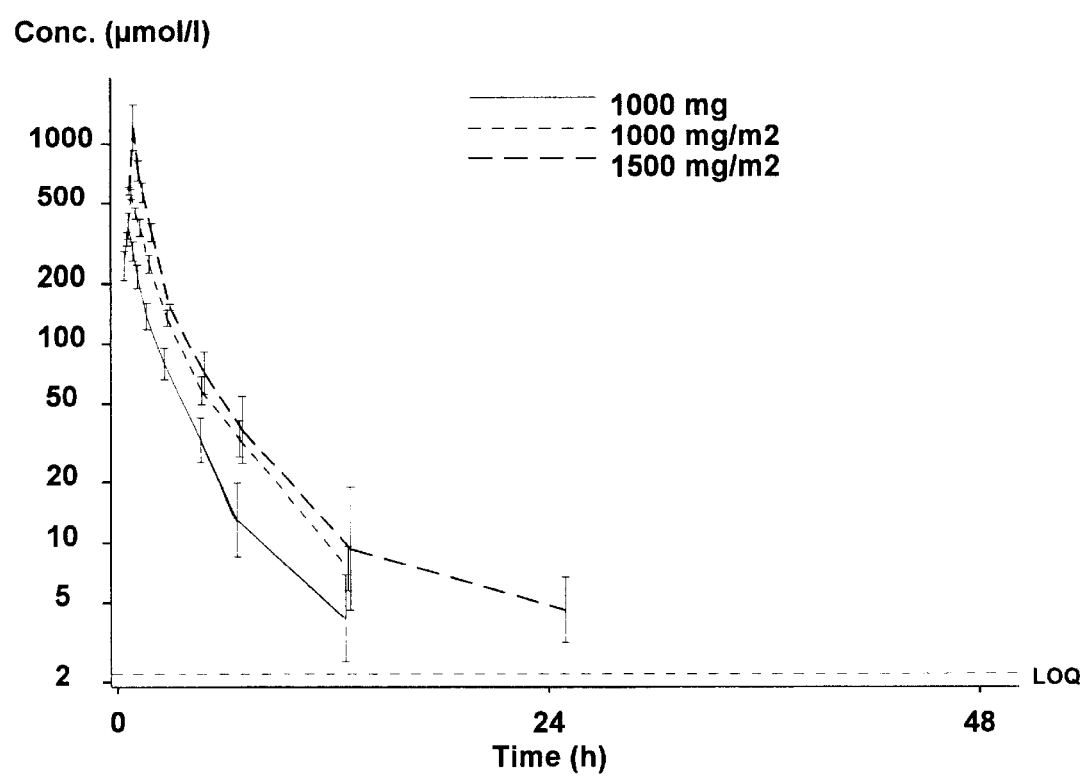
FIG. 1 illustrates the concentration of estramustine phosphate after a single intravenous dose of Estracyt (mean ±SEM, N=4+4+3) given at a dosage of 1000 mg (range 980–1070 mg), 1000 mg/m², and 1500 mg/m².

The present invention describes methods of potentiating the therapeutic use and efficacy of intravenously administered estramustine phosphate. It provides for the intravenous administration of estramustine phosphate in dosages exceeding 1300 mg. It also provides for intravenous administration of estramustine phosphate at dosages exceeding 950 mg/m² (milligrams per square meter of body surface area). It further provides for administration of high dose intravenous estramustine phosphate as a single dose, which may further be administered on a weekly or longer schedule. The present invention enables optimization of pharmacokinetics as to maximize therapeutic advantage, and further enables use of intravenous estramustine phosphate in combination with other therapies, including other chemotherapies, providing further improved therapeutic benefit. The present invention enables use of intravenous estramustine phosphate as therapy for multiple tumor types, including prostate, breast, lung, ovarian, colorectal, melanoma, pancreatic, and brain cancers.

Thus, one application of the present invention is to provide high dose estramustine phosphate therapy intravenously, wherein the dose exceeds 950 mg/m².

Another application is to provide a schedule of intravenous administration, whereby that schedule enables optimization of pharmacokinetics of estramustine phosphate and its metabolites at minimal toxicity, and further whereby said optimization permits convenient and efficacious combination regimens of therapy.

Thus, an application of the present invention permits the use of intravenous estramustine phosphate in combination with other therapeutic regimens, including cytotoxic chemotherapy.

Another application of the present invention is to provide a method which increases binding saturation and prolongs binding duration of estramustine phosphate or its metabolites to estramustine binding protein or estrarnustine binding protein-like protein (EMBP).

Thereby, the present invention provides application to treatment of cancers having EMBP, including but not limited to prostate, breast, lung, ovarian, colorectal, melanoma, pancreatic, and brain cancers, by intravenous administration.

Another application of the present invention is to provide a method of rapidly relieving symptoms secondary to cancer, inclusive of but not limited to cancer-induced pain and urinary obstruction.

Further, the present invention enables these applications for use of intravenous estramustine phosphate independent of the formulation. Thereby, the present invention provides for the infusion of estramustine phosphate as free drug, as proteinbound drug, or as drug within liposomes.

Thereby, the present invention describes a formulation of estramustine phosphate wherein the estramustine phosphate is administered intravenously in conjunction with liposomes.

Thus, the method of the present invention in which doses above 900 mg/M² (generally greater than 1300 mg per dose) can be administered safely and within an effective schedule is extremely unexpected.

The present invention teaches the advantage of intravenous estramustine in combination with other chemotherapy agents. The present invention further teaches the advantage of high dose intravenous estramustine in combination with other chemotherapeutic agents.

We teach in this invention that intravenous estramustine phosphate may be used to treat tumors having elevated EMBP-like protein (herein referred to simply as EMBP).

Figure 2:
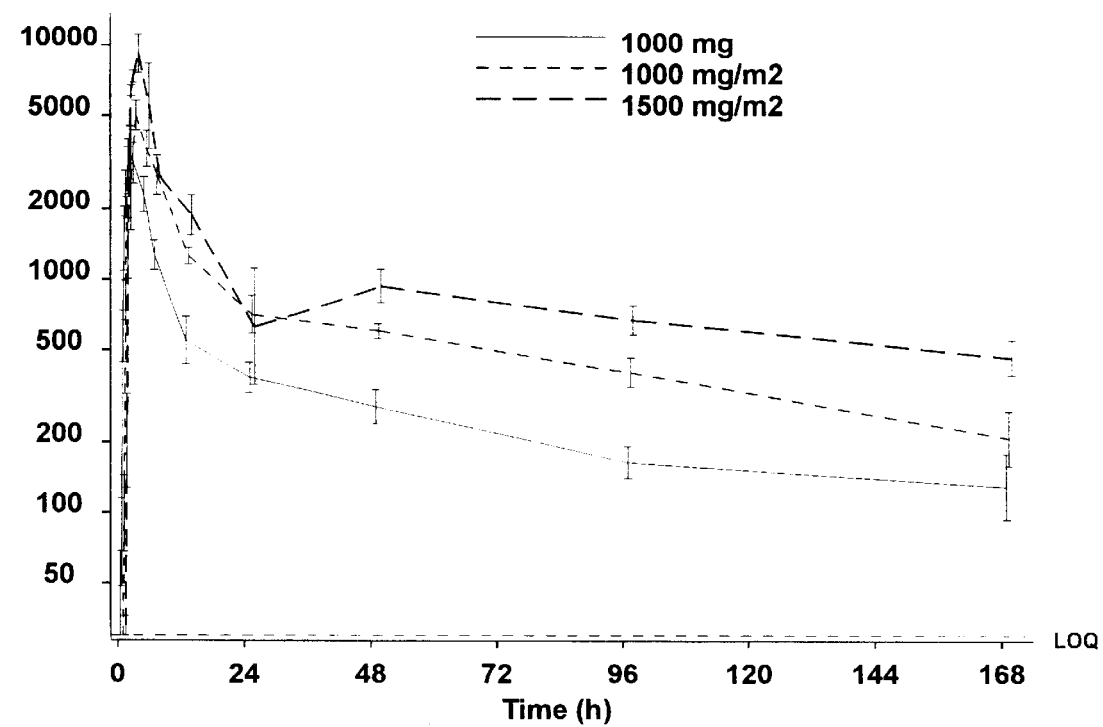
FIG. 2 illustrates the concentration of estromustine after a single intravenous dose of Estracyt (mean ±SEM, n=4+ 4+3) given at a dosage of 1000 mg (range 980–1070 mg), 1000 mg/m², and 1500 mg/m².

The novel and non-obvious applications of the present invention can be recognized from a comparison of the pharmacokinetic data following oral administration estramustine phosphate with that following high-dose intravenous administration of estramustine phosphate. The pharmacokinetic and toxicity data regarding high-dose intravenous estramustine phosphate is not known to the art. Dephosphorylation of estramustine phosphate to estramustine (EM), followed by oxidation at the 17 position to estromustine (EoM), the estrone analogue of EM, are the major metabolic steps after administration of oral estramustine phosphate in man. EoM is the predominant metabolite found in plasma when estramustine phosphate is administered on the daily oral schedule. The relative bioavailability based on estromustine is approximately 44%(Gunnarsson, 1984). After intravenous administration estramustine phosphate is initially found in plasma but is rapidly hydrolyzed to the same metabolites as are found after oral administration, the major metabolite being estromustine. Both estramustine and estromustine are further metabolized by cleavage of the carbamic ester to yield approximately 15% estradiol and estrone, respectively (Gunnarsson, 1981, 1984). We have demonstrated an unexpected prolonged availability of the major metabolite estromustine following high-dose intravenous administration, which can lead to unexpected clinical benefits. Previous data from patients treated with a single intravenous dose of 300 mg demonstrated that the elimination of estromustine had a half lives of 10–20 hours. The main route of elimination was metabolism of estromustine phosphate to estramustine, estromustine, estradiol and estrone. The data of particular importance for the efficacy of estramustine phosphate was the half lives of estramustine phosphate, (FIG. 1), and the major cytotoxic metabolite estromustine (FIG. 2). By application of the methods of this invention, we now demonstrate the novel finding that after a single high intravenous dose of estramustine phosphate at 1000 mg/m$^2$ it was found that the half life of estromustine was approximately 100 hours, (FIG. 2). This finding further enables therapeutic applications of high-dose intravenous estramustine phosphate.

DETAILED DESCRIPTION OF THE PREFERRED EMBODIMENTS

The present invention teaches the ability to administer estramustine phosphate at doses above 950 mg/m$^2$ (i.e., greater than 1300 mg).

The method of the present invention is performed as follows. In the preferred method, estramustine phosphate is administered at a single infusion dosage exceeding 950 mg/m$^2$. Intravenous administration is performed either through a central or peripheral intravenous route. During preparation of the intended drug, the contents of packaged estramustine phosphate intended for intravenous usage are dissolved, wherein the packaged contents may consist of but are not limited to a lyophilized powder of the meglumine salts in vials of estramustine phosphate, or similar freeze-dried estramustine phosphate which are first dissolved in sterile water such as 5 ml sterile water per 300 mg estramustine phosphate, or in 5% dextrose in water for intravenous administration. In the preferred method, 5% dextrose in water is used as the diluent. In the preferred method, during preparation of the dissolved drug the preparation should not be shaken, but should be slowly inverted to mix. The solution is then given as an intravenous infusion with the preferred duration of infusion time being 30 minutes to 3 hours, whereby infusion over 1–2 hours is a safe and convenient method. Saline solution may result in drug precipitation and thereby its use is not preferred in the infusion.

When estramustine phosphate is administered through a peripheral intravenous route, it is preferred that a longer duration of infusion and greater total infusional volume be utilized to minimize vascular irritation. Alternatively, the estramustine phosphate solution can be mixed with various amounts but preferably 3–5% human albumin or other plasma proteins including synthetic plasma proteins to achieve protein binding of the estramustine phosphate and therefore minimize any potential vascular damage.

The invention may be further realized using other preparations or formulations of estramustine phosphate. One particularly advantageous preparation of the chemotherapeutic agent estramustine phosphate which enables infusion of estramustine phosphate through either a peripheral or central vein, both at high doses and also doses less than 1300 mg, involves the infusion of estramustine phosphate in conjunction with liposomes (herein referred to as liposome encapsulated estramustine phosphate or liposomal estramustine). In one preferred method of preparing liposomal estramustine, estramustine phosphate solution is first prepared in the manner described above and then injected into a vial containing empty liposomes available as a lyophilized powder. Following adequate hydration of the liposomes, the vials are vortexed and sonicated, followed by infusion into the patient.

When estramustine phosphate is administered through a central venous route, said administration may be performed through either a temporary or permanent venous access device, including but not limited to a triple lumen catheter, Hickman catheter, subclavian line, jugular line, or mediport. Said administration may be but is not necessarily performed concomitant with anticoagulant therapy or with the addition of varying amounts but preferably 3–5% human albumin or other plasma proteins or liposomal estramustine to minimize any potential vascular damage in a given patient.

While the dosage of estramustine phosphate in the present invention is greater than 1300 mg, it is preferred that the patient be treated at a dose exceeding 950 mg/m$^2$. Thereby, one preferred method is to administer a single intravenous dosage of 1000 mg/m$^2$. Another preferred method is to administer a single intravenous dosage of 1500 mg/m$^2$. Furthermore, a dosage of 2000 mg/m$^2$ may be administered. However, the invention is inclusive of other dosages above 950 mg/m$^2$ and the preferred dosages are not to imply limitation.

The most preferred schedule of estramustine phosphate administration in the invention is a single infusion given once weekly to a maximal dose of 4000 mg or 3500 mg/m$^2$. Another preferred schedule is administration of a single drug infusion once every two weeks. Another preferred schedule is administration of a single drug infusion once every three weeks. Another preferred schedule is administration of a single drug infusion once every four weeks. One schedule may be preferred over another in consideration of schedules with other concomitant therapy. These schedules may repeat in a serial or repetitive fashion.

The invention described herein enables methods to prolong blood and/or tissue levels at high elevations for estramustine phosphate metabolites, including estromustine, estramustine, estrone and estradiol. Thereby, enhanced synergistic interactions with other therapies is enabled, wherein such other therapies include but are not limited to chemotherapy, radiotherapy, monoclonal antibodies, and biologic herapies. The present invention provides maximization of therapeutic benefit by rolongation of elevated blood and tissue levels of estramustine phosphate and its etabolites. Thereby, maximization of therapeutic benefit is achieved wherein estramustine phosphate is administered intravenously at dosages exceeding 950 mg/m$^2$, which are administered in combination with other cancer therapies, inclusive but not limited to radiotherapy, chemotherapy, monoclonal antibodies, and biologic therapies.

In the preferred method, therapeutic benefit is potentiated by administering intravenous estramustine phosphate at single dosages exceeding 950 mg/m$^2$, with other cytotoxic chemotherapies. In the preferred method said combination is achieved by administering intravenous estramustine phosphate within 3 days of the other chemotherapeutic agents, preferably on the day of, or the day prior to administration of the other chemotherapeutic agents. A particularly preferred method is achieved when the other chemotherapeutic agents consist of anti-mitotic agents or antimicrotubule agents, inclusive of but not limited to taxanes, including taxol and taxotere, and agents including vinblastine, vincristine, etoposide, navelbine, doxorubicin, irinotecan (CPT-11), and liposome encapsulated chemotherapeutic agents, including liposome encapsulated taxanes such as liposome encapsulated paclitaxel. It may be further beneficial if a combination with a monoclonal therapy is utilized, that the monoclonal agent include a radionucleotide or an anti-growth factor agent.

Plasma or serum levels of estromustine are further sustained when estramustine phosphate is administered intravenously as a single infusion at a dosage exceeding 950 mg/m$^2$ The infusion may optionally be repeated in a serial or repetitive manner to maintain elevated blood levels of the estromustine phosphate metabolites. Sustained levels of estramustine phosphate and its metabolites thereby enable sustained therapeutic benefit.

The present invention thereby provides a method to increase the binding saturation of estramustine or its metabolites to estramustine binding protein or likeprotein protein by administering estramustine phosphate intravenously at a single infusion dose exceeding 950 mg/m$^2$. Similarly, the binding duration of estramustine phosphate or its metabolites to estramustine binding protein or estramustine binding protein-like protein (EMBP) is increased in the invention by administering the drug at intravenous dosages exceeding 950 mg/m$^2$. Thereby, all cancers having either estramustine binding protein or estramustine binding protein like-protein may be treated by intravenous estramustine phosphate. It is particularly preferred to treat prostate cancer in such manner. It is further preferred to treat breast cancer, melanoma, lung cancer. pancreatic cancer, colorectal cancer, ovarian cancer, and cancers of the brain in such manner. It is particularly preferred that estramustine phosphate be administered intravenously wherein the single dosage exceeds 950 mg/m$^2$ when treating cancers having either estramustine binding protein or estramustine binding protein likeprotein, inclusive of but not limited to the group of cancers including prostate cancer, breast cancer, ovarian cancer, pancreatic cancer, melanoma, lung cancer, and cancers of the brain.

Said cancers may further be treated using liposomal estramustine, either as a single agent or in combination with other chemotherapies. Said administrations are preferably repeated in serial or repetitive fashion at schedules of the invention, with or without combination of other therapies. Thus, said schedules may include combinational treatment of intravenous estramustine phosphate with other chemotherapeutic therapies given on a once weekly, a once every two week, a once every three week, or a once every four week schedule, and variations therein.

It is particularly preferred that intravenously administered estramustine phosphate be administered in combination with other chemotherapeutic cytotoxic agents when used in the treatment of prostate cancer, breast cancer, melanoma, lung cancer, pancreatic cancer, colorectal cancer, ovarian, and cancers of the brain. It is further particularly preferred that intravenously administered estramustine phosphate be administered in combination with radiation when used in the treatment of prostate cancer, breast cancer, lung cancer, pancreatic cancer, colorectal cancer, and cancers of the brain. It is further preferred that in treating cancers having estramustine binding protein or estramustine binding protein like-protein, including prostate cancer, breast cancer, lung cancer, pancreatic cancer, colorectal cancer, ovarian cancer, and cancers of the brain, estramustine phosphate be administered at intravenous dosages exceeding 950 mg/m$^2$ when used in combination with other cancer therapies.

The present invention enables both objective and subjective therapeutic benefit. Benefit achieved may relate to reduction of tumor size, improved quality of life, reduction of tumor obstruction, such as urinary obstruction, reduction of cancer-induced pain, improved survival, reduction in time to cancer recurrence, or other evidence of improvement. In particular, rapid objective or subjective therapeutic benefit is achieved by administering estramustine phosphate intravenously at a dosage exceeding 950 mg/m$^2$, either as a single agent or preferably in combination with other cancer therapies. Thereby the invention enables rapid relief of cancer-induced urinary obstruction, and rapid relief of cancer-induced pain.

Other features of the invention will become apparent in the course of the following descriptions of exemplary embodiments which are given for illustration of the invention and are not intended to be limiting thereof.

EXAMPLES

The following clinical cases are provided by way of example and not limitation.

Example 1

Two patients with advanced metastatic prostate cancer were treated with estramustine phosphate intravenously given through a central line. The patients received an estramustine phosphate dosage of 2500 mg/m$^2$. Estramustine phosphate was administered as a single infusion on a weekly schedule in a repetitive fashion. Each infusional dose was administered over a 90 minute infusion. The infusions were well tolerated without serious toxicity and both patients demonstrated a response (reduction) in their prostate specific antigen (PSA).

Example 2

Three patients with advanced metastatic prostate cancer were treated with estramustine phosphate administered intravenously through a central line at a dosage of 1000 mg/m$^2$. Estramustine phosphate was administered as a single infusion on a weekly schedule in a repetitive fashion. Each infusional dose was administered over a 30 minute infusion. The infusions were well tolerated with several patients demonstrating PSA response.

Example 3

Three patients with advanced metastatic prostate cancer were treated with estramustine phosphate administered intravenously through a central line at a dosage of 1500 mg/m². Estramustine phosphate was administered as a single infusion on a weekly schedule in a repetitive fashion. The infusional dose was administered either over 30 minutes or over 1 hour. The infusions were well tolerated with one patient demonstrating a response in bulky tumor adenopathy.

Example 4

Three patients with advanced metastatic prostate cancer were treated with estramustine phosphate intravenously given through a central line. The patients received an estramustine phosphate dosage of 2000 mg/m². Estramustine phosphate was administered as a single infusion on a weekly schedule in a repetitive fashion. Each infusional dose was administered over a 60 minute infusion. An anti-thrombotic agent was additionally administered for venous thrombosis prophylaxis. The estramustine phosphate infusions were well tolerated without serious toxicity, and with evidence of PSA response.

REFERENCES

Andersson S B, Lundgren R, Svensson L: Gas chromatographic determination of four metabolites of estramustine phosphate on plasma. Acta Pharm Suec 19:1–10, 1982

Batra S, Karlsson R, Witt L: Potentiation by estramustine of the cytotoxic effect of vinblastine and doxorubicin in prostatic tumor cells. Int J Cancer 68:1–6, 1996

Bergenheim A T, Gunnarsson P O, Edman K, von Schoultz E, Hariz M I Henriksson R: Uptake and retention of estramustine and the presence of estramustine binding protein in malignant brain tumors in humans. Br J Cancer 67:358–361, 1993 Bergh J, Björk P, Westlin J-E, Nilsson S: Expression of an Estramustine-binding associated protein in human lung cancer cell lines. Cancer Res 48:4615–4619, 1988

Björk P, Borg A, FernöM, Nilsson S: Expression and partial characterization of estramustine-binding protein (EMBP) in human breast cancer and malignant melanoma. Anticancer Res 11(3):1173–1182, 1991

Björk P, Jönsson U, Andrén-Sandberg Å: Binding sites for the cytotoxic metabolites of Estramustine phosphate (Estracyt®) in rat and human pancreas that are distinct from pancreatic Estrogen-binding protein. Pancreas 6:1:77–89, 1991

Dahllöf B, Hartley-Asp B, Billström A, Cabral F: Estramustine depolymerizes microtubules by binding to tubulin. Cancer Res 53:4573–4581, 1993

Edgren M, Westlin J E, Letocha H et al.: Estramustine-binding protein (EMBP) in renal cell carcinoma immunohistochemistry, immunoscintigraphy and in vitro estramustine effects. Acta Oncol 35(4):483–488, 1996

Eklöv S et al., Evidence for a non-estrogenic cytostatic effect of estramustine on human prostatic carcinoma cells in vivo. The Prostate 20:43–50, 1992

Eklöv S, Mahdy E, Wester K et al.: Estramustine-binding protein (EMBP) content in four different cell lines and its correlation to estramustine induced metaphase arrest. Anticancer Res 16(4A): 1819-1822, 1996

Flüchter S, Nelde H J, Björk P et al.: Effect of treatment on the expression of estramustine-binding protein (EMBP) in prostatic cancer patients: An immunohistochemical study. The Prostate 14:27–43, 1989

Forsgren B, Björk P, Carlstrom K, Gustafsson J Å, Pousette Å, Högberg B: Purification and distribution of a major protein in rat prostate that binds estramustine, a nitrogen mustard derivative of estradiol-17β. Proc. Natl. Acad. Sci USA: 76:3149–3153,1979

Gunnarsson P O, Andersson S-B, Johansson S-Å et al.: Pharmacokinetics of estramustine phosphate (Estracyt®) in prostatic cancer patients. Eur J Clin Pharmacol 26:113–119, 1984

Gunnarsson P O, Plym Forshell G, Fritiofsson Å, Norlen B J: Plasma concentration of Estramustine phosphate and its major metabolites in patients with prostatic carcinoma treated with different doses of Estramustine phosphate (Estracyt®). Scand J Urol Nephrol 15:201–206, 1981

Hartley-Asp B: Estramustine induced mitotic arrest in two human prostatic carcinoma cell lines DU 145 and PC-3. The Prostate 5:93–100, 1984

Hartley-Asp B, Gunnarsson P O: Growth and cell survival following treatment with estramustine, nor-nitrogen mustard, estradiol and testosterone of a human prostatic cancer cell line (DU 145). J Urology 127:818–822, 1982

Hudes G, Obasaju C, Chapman A, Gallo J, McAleer C, Greenberg R: Phase I study of Paclitaxel and Estramustine: Preliminary activity in hormone refractory prostate cancer. Sem Oncol, Vol 22:3, Suppl 6:6–11, 1995

Hudes G R, Greenberg R, Krigel R L, Fox S, et al.: Phase II study of estramustine and vinblastine, two microtubule inhibitors, in hormone-refractory prostate cancer. J Clin Oncol 10: 1754-1761, 1992

Keren-Rosenberg, S, Muggia, F M: Response to estramustine phosphate and paclitaxel in patients with advanced breast cancer: A phase I Study Seminars in Oncology 24:5 S3-26-S3-29, 1997

Lindberg B: Treatment of rapidly progressing prostatic carcinoma with Estracyt. Journal of Urol 108:303–305, 1972

Maier U, Hienert G, Simak R: Estramustine phosphate in secondary hormone-resistant carcinoma of the prostate. Eur Urol 17:216–218, 1990

Mareel M M, Storme G A, Dragonetti C H, De Bruyne G K, Hartley-Asp B, Segers J L, Rabaey M L. Antiinvasive activity of estramustine on malignant $MO_4$ mouse cells and DU 145 human prostate carcinoma cells in vitro. Cancer Res 48:1842–1849, 1988

Murphy G P, Slack N H, Mittleman A: Experiences with Estramustine Phosphate (Estracyt, Emcyt) in prostate cancer. Seminars in oncology 10(3) Suppl 3, 34–42, 1983

Nagel R, Kölln C-P: Treatment of advanced carcinoma of the prostate with estramustine phosphate. British Journal of Urol 49:73–79,. 1977

Norlen, B. J., Andersson S. B., Björk P., Gunnarsson P. O., Fritjofsson Å. Uptake of Estramustine phosphate (Estracyt) metabolites in prostate cancer. Journal of Urology 140:1058–1062, 1988

Petrylak D P, Shelton G B, Mac Arthur R B et al.: Phase I trial of Docetaxel—Estramustine in androgen insensitive prostate cancer. Cancer Investigation 16, Supp 1 p 62, 1997

Pienta K J, Lehr J E: Inhibition of prostate cancer growth by estramustine and etoposide: Evidence for interaction at the nuclear matrix. Journal of Urol 149:1622–1625,1993

Pienta K J, Redman B, Hussain M, Cummings G et al.: Phase II evaluation of oral estramustine and oral etoposide in hormone-refractory adenocarcinoma of the prostate. J Clin Oncol 12:2005–2012, 1994

Seidman A D, Scher H I, Petrylak D, Dershaw D D, Curley T: Estramustine and vinblastine: Use of prostate specific antigen as a clinical trial end point for hormone refractory prostatic cancer. J Urol 147:931–934, 1992

Speicher L A, Barone L, Tew K D: Combined antimicrotubule activity of estramustine and Taxol in human prostatic carcinoma cell lines. Cancer Res 52:4433–4440,1992

Stearns M, Tew K D: Estramustine binds MAP-2 to inhibit microtubule assembly in vitro. J Cell Science 89:331–342, 1988 von Schoultz E, Carlstrom K, Henriksson R et al.: Estrarnustine binding protein in primary tumors and metastases of malignant melanoma. Melanoma Res 4(6):401–405, 1994

Walz P H, Björk P, Edman K, Gunnarsson P O, Hartley-Asp B: Uptake and distribution of the estramustine-phosphate metabolite estramustine after single-dose injection in patients with prostatic cancer. Akt Urol 27:92–93, 1996

Lundgren, R. Estracyt intravenost for behandling av hormonreftraktarprostatacancer: Svenska Lakaresallskapets Rikstamma, 1995

This application is based on U.S. Provisional Application Ser. No. 60/079,542, which was filed on Mar. 27, 1998, which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A method of administering estramustine phosphate as an intravenous dose, whereby the dosage of a single infusion exceeds 1300 mg.

2. A method of administering estramustine phosphate as an intravenous dose, whereby the dosage of a single infusion exceeds 950 mg/m$^2$.

3. The method of claims 1 or 2, wherein estramustine phosphate is administered as a single infusion on a once weekly schedule.

4. The method of claims 1 or 2, wherein estramustine phosphate is administered as a single infusion on a once every two week schedule.

5. The method of claims 1 or 2, wherein estramustine phosphate is administered as a single infusion on a once every three week schedule.

6. The method of claims 1 or 2, wherein estramustitle phosphate is administered as a single infusion on a once every four week schedule.

7. The method of claims 1 or 2, wherein estramustine phosphate is administered in combination with other anti-cancer therapies.

8. The method of claim 7, wherein estramustine phosphate is administered intravenously in combination with other chemotherapeutic agents.

9. The method of claim 1, wherein the infusion is given over 30 minutes to 3 hours.

10. The method of claim 2, wherein the infusion is given over 30 minutes to 3 hours.

11. A method of administering estramustine phosphate, wherein estramustine phosphate is first encapsulated within liposomes, and then administered intravenously.

* * * * *